(12) United States Patent
Granger et al.

(10) Patent No.: US 11,185,557 B2
(45) Date of Patent: Nov. 30, 2021

(54) USE OF RHAMNOSE AND DERIVATIVES THEREOF AS ANTIFUNGAL AGENTS

(71) Applicant: ISDIN, S.A., Barcelona (ES)

(72) Inventors: Corinne Jeanne Rose Granger, Barcelona (ES); Carlos Ramon Trullas Cabanas, Barcelona (ES)

(73) Assignee: ISDIN, S.A., Barcelona (ES)

( * ) Notice: Subject to any disclaimer, the term of this patent is extended or adjusted under 35 U.S.C. 154(b) by 33 days.

(21) Appl. No.: 16/634,523

(22) PCT Filed: Jul. 27, 2018

(86) PCT No.: PCT/EP2018/070512
§ 371 (c)(1),
(2) Date: Jan. 27, 2020

(87) PCT Pub. No.: WO2019/020822
PCT Pub. Date: Jan. 31, 2019

(65) Prior Publication Data
US 2020/0222445 A1    Jul. 16, 2020

(30) Foreign Application Priority Data
Jul. 28, 2017 (EP) .................................. 17382512

(51) Int. Cl.
*A61K 31/715* (2006.01)
*A61P 31/10* (2006.01)
*A61K 31/4412* (2006.01)
*A61K 31/7004* (2006.01)

(52) U.S. Cl.
CPC ........ *A61K 31/715* (2013.01); *A61K 31/4412* (2013.01); *A61K 31/7004* (2013.01); *A61P 31/10* (2018.01)

(58) Field of Classification Search
CPC .............................. A61K 31/715; A61P 31/10
See application file for complete search history.

(56) References Cited

U.S. PATENT DOCUMENTS

2008/0200427 A1   8/2008   Gatto

FOREIGN PATENT DOCUMENTS

| CN | 104342324 A | 2/2015 | |
|---|---|---|---|
| EP | 1949887 A2 | 7/2008 | |
| JP | H08-333213 | * 12/1996 | ............. A01N 63/00 |
| JP | H11-255621 | * 9/1999 | ............. A61K 31/19 |
| KR | 2010/0026835 A | 3/2010 | |
| KR | 2010/0060599 A | 6/2010 | |
| WO | WO 2014/044779 A2 | 3/2014 | |

OTHER PUBLICATIONS

English machine translation of JPH11-265621, downloaded from worldwide.espacenet.com (Year: 1999).*
English machine translation of JPH08-333213, downloaded from worldwide.espacenet.com (Year: 1996).*
Schwartz et al., "Seborrheic Dermatitis: An Overview" American family Physician vol. 74 No. 1 pp. 125-130 (Year: 2006).*
Milani, M., Barrier Repair Therapy in Atopic Eczema: New Evidences in Improving Skin Functions with Topical Emolliency and Hydration Strategies J Clin Dermatol Ther vol. 5 No. 2 pp. 1-4, DOI: 10.24966/CDT-8771/100011 (Year: 2015).*
DeAngelis et al., "Three Etiologic Facets of Dandruff and Seborrheic Dermatitis: Malassezia Fungi, Sebaceous Lipids, and Individual Sensitivity" J Investig Dermatol Symp Proc vol. 10 pp. 295-297 (Year: 2005).*
Sahraie-Rad et al., "Preparation of Strong Antidandruff Shampoo Using Medicinal Plant Extracts: A Clinical Trial and Chronic Dandruff Treatment" Jundishapur J Nat Pharm Prod. vol. 10 No. 4 pp. 1-8, doi: 10.17795/jjnpp-21517 (Year: 2015).*
Andres et al., "Pharmacological properties of rhamnose-rich polysaccharides, potential interest in age-dependent alterations of connectives tissues" Pathologie Biologie vol. 54 pp. 420-425 doi:10.1016/j.patbio.2006.07.004 (Year: 2006).*
Ravelojaona et al., "Protection by rhamnose-rich polysaccharides against the cytotoxicity of Maillard reaction products" Biomedicine and Pharmacotherapy vol. 60 pp. 359-362 doi:10.1016/j.biopha.2006.06.019 (Year: 2006).*
Granger et al., "Ex-vivo determination of antifungal activity of a new prescription nonsteroidal facial cream against Malassezia furfur in human skin explants" Fall Clinical Dermatology Conference® Oct. 12-15, 2017. Las Vegas, Nevada, USA (Year: 2017).*
International Search Report and Written Opinion dated Oct. 31, 2018 for PCT Application No. PCT/EP2018/070512, 15 pages.
Chowdhry, et al: "Topical antifungals used for treatment of Seborrheic dermatitis", Jan. 6, 2017, MedCrave, Journal of Bacteriology & Mycology: Open Access 2017, vol. 4, No. 1, pp. 1-8, XP-055430371.
Molina, et al: "Glico-Cosmetologia Polisaccaride ranmosilato antinfiammatorio", Cosmetic Technology 2004, Jan. 1, 2004, vol. 7, No. 2, pp. 29-53, XP009501591, with abstract.

* cited by examiner

*Primary Examiner* — Eric Olson
(74) *Attorney, Agent, or Firm* — Squire Patton Boggs (US) LLP

(57) ABSTRACT

It relates to a rhamnose or a rhamnose-rich polysaccharide for use in the treatment and/or prevention of fungal infections in human beings. It also relates to a combination of rhamnose or a rhamnose-rich polysaccharide and a further antifungal agent for use in the treatment and/or prevention of fungal infections in human beings. It also relates to pharmaceutical or cosmetic composition comprising an effective amount of rhamnose or a rhamnose-rich polysaccharide for use in the treatment and/or prevention of fungal infections in human beings.

13 Claims, 2 Drawing Sheets

USE OF RHAMNOSE AND DERIVATIVES THEREOF AS ANTIFUNGAL AGENTS

This application is a National Stage Application of International Application No. PCT/EP2018/070512 filed 27 Jul. 2018 which claims the benefit of EP application EP 17382512.6, filed on 28 Jul. 2017. EP application 17382512.6 is incorporated herein by reference in its entirety.

TECHNICAL FIELD

The present invention relates to the use of rhamnose or a rhamnose-rich polysaccharide in the treatment and/or prevention of fungal infections in human beings, in particular fungal infections caused by *Malassezia* species that are associated to skin diseases. It also relates to the use of pharmaceutical and cosmetic compositions containing rhamnose or a rhamnose-rich polysaccharide in the treatment and/or prevention of fungal infections in human beings.

BACKGROUND ART

Seborrheic dermatitis (SD) is a common chronic-recurrent inflammatory skin disease that affects around 1-3% of the population, mostly adults. SD causes scaly, itchy, red skin on the scalp, eyebrows, nasolabial creases, lips, ears, sternal area, axillae, submammary folds, umbilicus, groins, and gluteal crease. The disease is characterized by many shapes, sizes, and surface textures and is often crust-like, yellowish, and accompanied by itching.

It has been described that proliferation of *Malassezia* species is an important contributing factor to seborrheic dermatitis. *Malassezia* species are opportunistic pathogenic fungi. Most of them are lipid dependent, a property that is compensated by breaking down host sebum into fatty acids by lipases. *Malassezia furfur* is a commensal species of yeast found primarily around hair follicles on sebum-rich areas of the body. It obtains the fatty acids on which it depends by producing lipases that hydrolyze triglycerides. These fatty acids may irritate the skin and cause scaling or may contribute to inflammation, further leading to seborrheic dermatitis.

A variety of treatments including topical corticosteroids (e.g. hydrocortisone 1%), topical antifungal agents (e.g. ketoconazole 2%, ciclopirox 1%), and topical calcineurin inhibitors (e.g. pimecrolimus 1%) have been used for the treatment of SD.

Despite of the existence of the above treatments, they are often not fully satisfactory due to the high incidence of recurrence of skin surface mycoses. Further, in some cases these compounds exhibit an intrinsic toxicity that limits their applicability. A substantial number of patients still do not benefit from using prior art treatments, either because they do not respond to the treatment, or because they do not tolerate a particular treatment. Besides, the frequent use of the antifungals in these pathologies could produce an increase in the fungic resistance to these drugs Based on these findings, there is still a need for active agents that show activity against *Malassezia* yeasts and overcome the problems of the prior art treatments, in particular in terms of efficacy, safety, and reduction of recurrence.

SUMMARY OF INVENTION

The inventors have unexpectedly found that rhamnose or rhamnose-rich polysaccharides have antifungal activity, in particular against *Malassezia* species. To the knowledge of the inventors, rhamnose-rich polysaccharides have only been described as anti-inflammatory agents and have been used in topical compositions for attenuating skin inflammation.

Additionally, the inventors have discovered that when rhamnose or a rhamnose-rich polysaccharide is used in combination with further antifungal agents a synergistic effect is obtained. As illustrated in the examples of the invention, the exemplified compositions showed very good antifungal activity at a lower dose of antifungal (about 0.5%) as compared to a well-known drug in this field (ketoconazole 2%). The reduction of the amount of antifungal agent allows improving the safety profile of the composition and reducing potential toxicity problems. Without being bound to theory, it is believed that the antifungal effect of the rhamnose or rhamnose-containing polysaccharides of the invention takes place through a different mechanism of action as compared to other known antifungal agents, such as ketoconazole.

Thus, the invention relates to a rhamnose or a rhamnose-rich polysaccharide for use in the treatment and/or prevention of fungal infections in human beings.

It also relates to a combination of rhamnose or a rhamnose-rich polysaccharide and a further antifungal agent for use in the treatment and/or prevention of fungal infections in human beings.

It also relates to a pharmaceutical or cosmetic composition comprising an effective amount of rhamnose or a rhamnose-rich polysaccharide for use in the treatment and/or prevention of fungal infections in human beings, together with one or more pharmaceutically acceptable excipients or carriers.

DETAILED DESCRIPTION OF THE INVENTION

Figure 1:
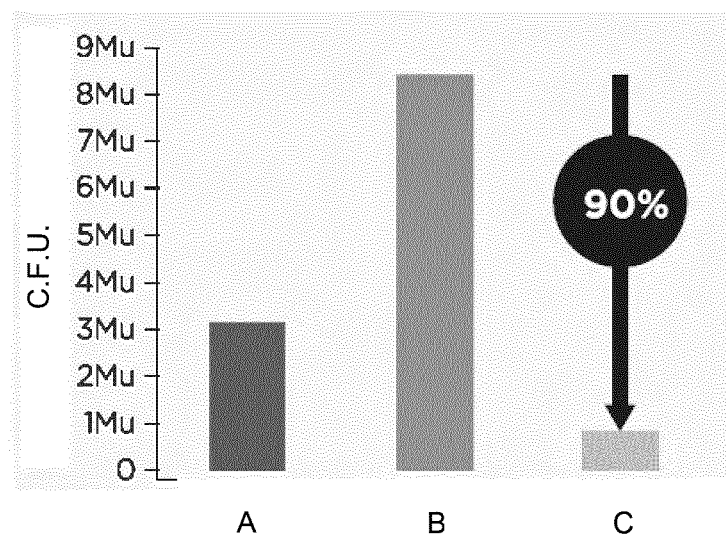
FIG. 1 shows an ex-vivo determination of the antifungal activity of the composition of example 1 against *Malassezia furfur* in human skin explants. Before inoculum (A). Untreated skin at day 0 (B). Skin treated with the composition of example 1 (C).

All terms as used herein in this application, unless otherwise stated, shall be understood in their ordinary meaning as known in the art. Other more specific definitions for certain terms as used in the present application are as set forth below and are intended to apply throughout the description and claims.

Unless otherwise stated, all percentages mentioned herein regarding the components of the composition are expressed in weight with respect to the total weight of the composition, provided that the sum of the amounts of the components is equal to 100%.

As mentioned above, the invention relates to a rhamnose or a rhamnose-rich polysaccharide for use in the treatment and/or prevention of fungal infections in human beings.

Rhamnose is a naturally occurring deoxy sugar that occurs in nature in its L-form as L-rhamnose (6-deoxy-L-mannose).

In one embodiment, optionally in combination with one or more features of the various embodiments described above or below, the rhamnose is L-rhamnose.

In another embodiment, optionally in combination with one or more features of the various embodiments described above or below, the rhamnose-rich polysaccharide comprises rhamnose, more particularly L-rhamnose, in an amount equal or higher than 40% w/w. More particularly, the rhamnose-rich polysaccharide comprises rhamnose in an amount from 40% to 60%, more particularly from 45 to 55%, and even more particularly about 50% w/w.

In another embodiment, optionally in combination with one or more features of the various embodiments described above or below, the rhamnose-rich polysaccharide comprises a repeating unit of formula (I)

It forms also part of the invention a combination comprising rhamnose or a rhamnose-rich polysaccharide as previously, and a further antifungal agent for use in the treatment and/or prevention of fungal infections in human beings. Thus, in one embodiment, optionally in combination with one or more features of the various embodiments described above or below, the rhamnose or a rhamnose-rich polysaccharide forms part of a combination comprising a further antifungal agent.

Non-limiting examples of further antifungal agents include, miconazol, climbazol, ketoconazol, piroctone olamine, zinc pyrithione, selenium sulphide, ciclopirox olamine, and the like.

In one embodiment, optionally in combination with one or more features of the various embodiments described above or below, the further antifungal agent is selected from the group consisting of miconazol, climbazol, ketoconazol,

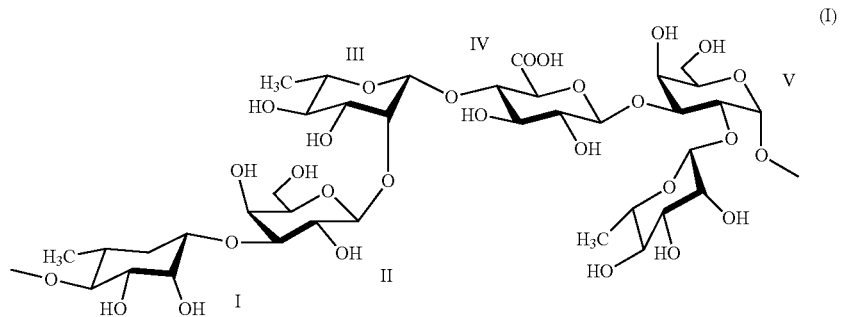

(I)

The above repeating unit of formula (I) is formed from units of rhamnose (I, III, VI), galactose (II, V) and glucuronic acid (IV). Thus, about 50% w/w of the polysaccharide is rhamnose.

In another embodiment, optionally in combination with one or more features of the various embodiments described above or below, the rhamnose-rich polysaccharide has a molecular weight from 45000 to 55000 g/mol, more particularly from 47000 to 52000 g/mol, even more particularly from 49000 to 51000 g/mol, and even more particularly about 50000 g/mol.

For the purposes of the present invention, the term "molecular weight" refers to the weight average molecular weight (Mw). Said molecular weight can be calculated by methods well known in the art such as viscometry, ultrafiltration vapor pressure and size exclusion chromatography (GPC/SEC).

In one embodiment, optionally in combination with one or more features of the various embodiments described above or below, the rhamnose-rich polysaccharide forms part of an aqueous solution and is present in the solution in an amount from 1 to 4% w/w, more particularly in an amount about 2.5% w/w.

In another embodiment, optionally in combination with one or more features of the various embodiments described above or below, the aqueous solution containing the rhamnose polysaccharide is the commercially available Rhamnosoft (Solabia). Rhamnosoft (INCI name: Biosacharide gum-2, CAS Registry Number 758716-52-81) is an aqueous solution containing the polysaccharide having the repeating unit of formula (I) as described above in an amount of about 2.5% w/w. The polysaccharide in Rhamnosoft has about 50000 g/mol contains L-rhamnose, D-Galactose and glucuronic acid.

piroctone olamine, zinc pyrithione, selenium sulphide, and ciclopirox olamine. More particularly, the further antifungal agent is piroctone olamine.

In another embodiment, optionally in combination with one or more features of the various embodiments described above or below, the rhamnose or the rhamnose-rich polysaccharide forms part of a pharmaceutical or cosmetic composition which comprises an effective amount of the rhamnose or rhamnose-rich polysaccharide, together with one or more pharmaceutically or cosmetically acceptable excipients or carriers. In a particular embodiment, the composition is a pharmaceutical composition. In another particular embodiment, the composition is a cosmetic composition.

In one particular embodiment, optionally in combination with one or more features of the various embodiments described above or below, in the pharmaceutical or cosmetic composition previously described either rhamnose or alternatively, the rhamnose-rich polysaccharide is the only saccharide present in the composition.

The expression "pharmaceutically or veterinary acceptable excipients or carriers" means that the excipients or carriers are suitable for the preparation of compositions for pharmaceutical or medical uses in humans and animals. Each component must be pharmaceutically acceptable in the sense of being compatible with the other ingredients of the pharmaceutical or veterinary composition. It must also be suitable for use in contact with tissues or organs of humans and animals without excessive toxicity, irritation, allergic response, immunogenicity or other problems or complications consistent with a reasonable risk/benefit relationship.

The expression "cosmetically acceptable excipients or carriers" means that the excipients or carriers are suitable for the preparation of compositions for cosmetic use. Each component must be cosmetically acceptable in the sense of being compatible with the other ingredients of the cosmetic composition. It must also be suitable for use in contact with tissues or organs of humans and animals without excessive toxicity, irritation, allergic response, immunogenicity or other problems or complications consistent with a reasonable risk/benefit relationship.

The expression "effective amount" as used herein, relates to the amount of product that provides the cosmetic or therapeutic desired effect after its application. The effective amount that provides a therapeutic effect (also cited here as therapeutically effective amount) is the amount of a compound that, when administered, is sufficient to prevent the development of, or to relieve to some degree one or more of the symptoms of the disease to which it is directed. The particular dose of compound administered according to this invention may vary according to the particular conditions surrounding the case, including the administered compound, the route and frequency of administration, age, condition of the patient, nature or severity of the condition, disorder or condition to be treated or prevented and similar considerations.

In one embodiment, optionally in combination with one or more features of the various embodiments described above or below, the amount of rhamnose in the compositions previously described is from 0.0002 to 1% w/w, from 0.0002 to 0.5% w/w, from 0.0002 to 0.07% w/w, from 0.005 to 1% w/w, from 0.005 to 0.5% w/w, from 0.01 to 0.07% w/w, from 0.0002 to 0.05% w/w, from 0.0002 to 0.01% w/w, from 0.0002 to 0.007% w/w, from 0.0002 to 0.005% w/w, from 0.0002 to 0.001% w/w, from 0.0004 to 0.0008% w/w, or about 0.000625% w/w.

In another embodiment, optionally in combination with one or more features of the various embodiments described above or below, the amount of rhamnose-rich polysaccharide in the compositions previously described is from 0.0004 to 2% w/w, from 0.0004 to 1% w/w, from 0.0004 to 0.15% w/w, from 0.01 to 2% w/w, from 0.01 to 1% w/w, from 0.02 to 0.15% w/w, from 0.0004 to 0.1% w/w, from 0.0004 to 0.02% w/w, from 0.0004 to 0.015% w/w, from 0.0004 to 0.01% w/w, from 0.0004 to 0.002% w/w, from 0.0008 to 0.0015% w/w, or about 0.00125% w/w.

In another embodiment, optionally in combination with one or more features of the various embodiments described above or below, the pharmaceutical or cosmetic composition comprising rhamnose or the rhamnose-rich polysaccharide is a topical composition.

For the purposes of the present invention, the term "topical" refers to the local administration of a compound or composition skin, skin appendages such as nails, oral and vaginal mucosa.

Generally, topical formulations include creams, emulsions (such as e.g.oil in water emulsions, water in oil emulsions, water in silicon emulsions), aqueous dispersions, milks, balms, foams, gels, ointments, lotions, cream gels, gel creams, hydroalcoholic solutions, hydro solutions, hydrogels, shampoos, conditioners, serums, pastes, pencils and vaporizers, sprays, including "leave on" formulations and "rinse-off" formulations, wherein the rhamnose or the rhamnose-rich polysaccharide is dispersed or dissolved in suitable excipients.

The topical compositions defined above comprise pharmaceutical or cosmetic excipients or carriers appropriate for topical administration, including, humectants, emollients, skin conditioning agents, film-forming agents, emulsifying agents, chelating agents, surfactants, viscosity controlling agents, pH adjusters, sunscreen agents, antioxidants, preservatives, solvents or mixtures thereof.

The excipients or carriers used have affinity for the skin, are well tolerated, are stable, and are used in an amount suitable to provide the desired consistency and ease of application. The appropriate excipients and/or carriers, and their amounts, can readily be determined by those skilled in the art according to the type of formulation being prepared.

Non-limiting examples of emulsifying agents include glyceryl stearate, PEG-100 stearate, Laureth-7, and sclerotium gum.

Examples of surfactants include, without limitation, perfluorooctanoate (PFOA or PFO), alkyl benzene sulfonate, soaps, fatty acid salts, or alkyl sulfate salts such as perfluorooctanesulfonate (PFOS), sodium dodecyl sulfate (SDS), ammonium lauryl sulfate, or sodium lauryl ether sulfate (SLES), alkyltrimethylammonium including cetyl trimethylammonium bromide (CTAB), or hexadecyl trimethyl ammonium bromide, cetylpyridinium chloride (CPC), polyethoxylated tallow amine (POEA), benzalkonium chloride (BAC), or benzethonium chloride (BZT). dodecyl betaine, cocamidopropyl betaine, or coco ampho glycinate, alkyl poly(ethylene oxide), alkylphenol poly(ethylene oxide), copolymers of poly(ethylene oxide), poly(propylene oxide) (commercially called Poloxamers or Poloxamines), alkyl polyglucosides including octyl glucoside and decyl maltoside, fatty alcohols including cetyl alcohol and oleyl alcohol, cocamide MEA, cocamide DEA, polysorbates including tween 20, tween 80, dodecyl dimethylamine oxide PEG-100 stearate.

Examples of viscosity controlling agents include, without limitation, synthetic polymers such as carbomers (cross linked polymers of acrylic acid) such as C10-30 Alkyl acrylate crosspolymer, cellulosic polymers such as hydroxypropyl methylcellulose, methylcellulose, sodium carboxy methylcellulose, and hydroxypropyl cellulose, sclerotium gum, xanthan gum and block copolymers based on ethylene oxide and propylene oxide (pluronic compounds), dimethicones such as vinyl dimethicone crosspolymer, and the like.

Examples of humectants include, without limitation, glycerin, diglycerin, ethylhexylglycerin, pentylene glycol, polyethylene glycol, propylene glycol, butylene glycol, sorbitol, sucrose, or threalose. Preferably, the humectant is selected group consisting of glycerin and butylene glycol, and their mixtures.

Examples of pH adjusters agents include, without limitation, monobasic sodium phosphate, dibasic sodium phosphate, benzoic acid, sodium citrate, triethanolamine, sodium hydroxide, lactic and citric acid, and the like.

Examples of antioxidant agents include, without limitation, ascorbic acid, ascorbyl palmitate, sodium ascorbate, sodium bisulfite, sodium sulfite, sodium metabisulfate, curcumin, tetrahydrocurcumin, diacetyl tetrahydrocurcum in, resveratrol, quercetin, hesperidin, myricetin, naringin, alpha-lipoic acid, monothioglycerol, butylated hydroxy anisole (BHA), butylated hydroxy toluene (BHT), propyl gallate, and the like.

Examples of solvents include, without limitation, ethanol, isopropyl alcohol, water, propylene glycol, polyethylene glycol, and the like.

Examples of chelating agents include, without limitation, disodium EDTA. Non-limiting examples of skin conditioning agents include stearyl glycyrrhtinate, pentylene glycol, and hydroxyphenyl propamidobenzoic acid. Non-limiting examples of film-forming agents include polyacrylamide, polymethyl methacrylate.

Non-limiting examples of emollients include C13-C14 isoparaffin, cyclohexasiloxane, cyclopentasiloxane, cetyl alcohol, isodecyl neopentanoate, almond oil, cetostearoyl alcohol, cetyl alcohol, cetyl esters wax, cottonseed oil, cyclomethicone, ethylene glycol palmitostearate, isopropyl myristate, isopropyl palmitate, lanolin, lecithin, light mineral oil, medium-chain triglycerides, mineral oil and lanolin alcohols, petrolatum, soybean oil stearyl alcohol, sunflower oil, xylitol and combinations thereof.

The election of the type of formulation will depend upon the nature of the active compound, the site of administration, the kinetics and duration of release of the compound of the invention, and the condition to be treated.

In another embodiment, optionally in combination with one or more features of the various embodiments described above or below, the composition previously defined comprises a further antifungal agent, more particularly piroctone olamine, even more particularly piroctone olamine in an amount from 0.2 to 1% w/w. Even more particularly, the composition previously defined comprises piroctone olamine in an amount from 0.3 to 0.7%, even more particularly about 0.5% w/w.

In another embodiment, optionally in combination with one or more features of the various embodiments described above or below, the rhamnose or the rhamnose-rich polysaccharide and the further antifungal agent are present in the composition previously defined in amounts producing a synergistic effect.

In another embodiment, optionally in combination with one or more features of the various embodiments described above or below, the total amount of antifungal agents in the composition as previously defined is equal or lower than 1% w/w, more particularly equal or lower than 0.8% w/w, and even more particularly equal or lower than 0.6% w/w.

In another embodiment, optionally in combination with one or more features of the various embodiments described above or below, the composition as previously defined comprises Zinc pyrrolidone carboxylate (Zinc PCA), piroctone olamine and stearyl glycyrrhetinate. More particularly, the composition as previously defined comprises from 0.3 to 1% w/w Zinc pyrrolidone carboxylate (Zinc PCA), from 0.3 to 0.7% w/w piroctone olamine and from 0.15 to 0.5% w/w stearyl glycyrrhetinate.

In one embodiment, optionally in combination with one or more features of the various embodiments described above or below, the composition of the invention as previously defined is a composition for scalp (scalp composition) or a composition for the nails (nail composition). Thus, it also form part of the invention hair products and nail products, which comprise an effective amount of rhamnose or a rhamnose-rich polysaccharide for use in the treatment and/or prevention of fungal infections in human beings, together with one or more pharmaceutically acceptable excipients or carriers.

Non-limiting examples of scalp products include sprays, mousses, gels, serums, oils, creams, lotions, shampoos, conditioners, powders, and the like.

Non-limiting examples of nail products include sprays, mousses, gels, serums, oils, creams, lotions, powders, nail gels, nail creams, nail polishes, nail lacquers and the like.

As mentioned above, the invention relates to rhamnose or a rhamnose-rich polysaccharide for use in the treatment and/or prevention of fungal infections in human beings. Thus, the invention also relates to the use of rhamnose or a rhamnose-rich polysaccharide as antifungal agents.

The invention also relates to the use of rhamnose or a rhamnose-rich polysaccharide, for the manufacture of a medicament or cosmetic composition for the treatment and/or prevention of fungal infections in human beings.

It also forms part of the invention a method for the treatment and/or prevention of fungal infections in human beings, comprising administering an effective amount of rhamnose or a rhamnose-rich polysaccharide, and one or more pharmaceutically or cosmetically acceptable excipients or carriers, in a subject in need thereof, including a human.

The invention also relates to the use of a combination comprising rhamnose or a rhamnose-rich polysaccharide, and a further antifungal agent for the manufacture of a medicament or cosmetic composition for the treatment and/or prevention of fungal infections in human beings.

It also forms part of the invention a method for the treatment and/or prevention of fungal infections in human beings, comprising administering an effective amount of a combination comprising rhamnose or a rhamnose-rich polysaccharide, and a further antifungal agent; and one or more pharmaceutically or cosmetically acceptable excipients or carriers, in a subject in need thereof, including a human.

In one embodiment, optionally in combination with one or more features of the various embodiments described above or below, the fungal infections are scalp fungal infections or nail fungal infections.

In one embodiment, optionally in combination with one or more features of the various embodiments described above or below, the antifungal infection is caused by *Malassezia* species. More particularly, the antifungal infection is caused by *Malasezzia furfur*.

In another embodiment, optionally in combination with one or more features of the various embodiments described above or below, the antifungal infection is associated with a skin disease. More particularly, the antifungal infection causes a skin disease. More particularly, the unbalanced microbiome including fungus causes a skin disease.

Non-limiting examples of diseases that can be treated and/or prevented include pityriasis versicolor, seborrheic dermatitis, dandruff, atopic dermatitis, psoriasis, folliculitis, gengivitis, blepharitis and onychomycosis.

In a more particular embodiment, optionally in combination with one or more features of the various embodiments described above or below, the skin disease is selected from the group consisting of pityriasis versicolor, seborrheic dermatitis, dandruff, atopic dermatitis, psoriasis, folliculitis, gengivitis, blepharitis and onychomycosis. Even more particularly, the skin disease is seborrheic dermatitis.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

Example 1

A cream having the composition indicated in the table below was prepared according to a process comprising the following steps:

1. Ingredients of phase A were mixed in the given order, with agitation after each addition until a homogeneous bulk was obtained. Then, the bulk was heated to 75-80° C.
2. Ingredients of phase B were weighed, heated to 75-80° C. and mixed until a homogeneous phase was obtained.
3. When both phases are at 75-80° C., phase B was slowly added to phase A and the mixture was homogenized.
4. The mixture obtained in step 3 was cooled down to 55° C., pH was adjusted with Sodium Hydroxide and the other ingredients of phase C was added in the given order, with agitation after each addition until a homogeneous bulk is obtained.
5. The mixture obtained in step 4 was cooled down to 20-30° C.

| Phase | Ingredient | Amount (% w/w) |
|---|---|---|
| A | Aqua (Water) | qst 100% |
|   | Glycerin | 13.06 |
|   | Disodium EDTA | |
|   | Acetamide MEA | |
|   | Sclerotium Gum | |
|   | Acrylates/C10-30 Alkyl Acrylate Crosspolymer | |
| B | Cetyl Alcohol | 12.00 |
|   | PEG-100 Stearate | |
|   | Cyclohexasiloxane | |
|   | Cyclopentasiloxane | |
|   | Dimethicone/Vinyl Dimethicone Crosspolymer | |
|   | Glyceryl Stearate | |
|   | Isodecyl Neopentanoate | |
|   | Stearyl Glycyrrhetinate | 0.30 |
| C | Sodium Hydroxide | 4.39 |
|   | Pentylene Glycol | |
|   | Butylene Glycol | |
|   | Hydroxyphenyl Propamidobenzoic Acid | |
|   | Ascorbyl Palmitate | |
|   | Polyacrylamide | |
|   | Polymethyl Methacrylate | |
|   | C13-C14 Isoparaffin | |
|   | Laureth-7 | |
|   | Biosaccharide Gum-2 | 0.05 |
|   | Piroctone Olamine | 0.50 |
|   | Zinc PCA (l-pyrrolidone carboxylate) | 0.60 |

Example 2 and Comparative Example 3

Creams having the composition indicated in the table below were prepared following the process described in example 1.

| Phase | Ingredient INCI Name | Amount (% w/w) Example 2 | Amount (% w/w) Comparative example 3 |
|---|---|---|---|
| A | Aqua | 85.13 | 82.68 |
|   | Glycerin | 7.00 | 7.00 |
| B | Isodecyl Neopentanoate | 7.00 | 7.00 |
|   | Cetyl Alcohol | | |
|   | Glyceryl Stearate | | |
|   | Peg-100 Stearate | | |
| C | Laureth-7 | 0.82 | 2.82 |
|   | Pentylene Glycol | | |
|   | Polyacrylamide | | |
|   | C13-14 Isoparaffin | | |
|   | Biosaccharide Gum-2 | 0.05 | — |
|   | Piroctone Olamine | — | 0.50 |
|   | Total | 100.00 | 100.00 |

Antifungal Activity Assay

Human organotypic skin cultures were obtained from abdominal skin removed during aesthetic surgery. These skin explants were altered by partial elimination of stratum corneum to facilitate the colonization and MF suspension was placed on the skin surface and incubated for 24 hours under conditions that are optimal for MF growth. 24 hours post initial MF inoculation, NSFC was topically applied on skin explants (2 mg/cm$^2$) and spread evenly. On control skin explants, inoculated in the same way, no product was applied (C2). A sham control group was treated with a neutral cream without known antifungal properties, petroleum jelly (P3). Growth of MF was monitored by quantifying MF Colony Forming Units (CFUs) in a sample removed from skin surface. The quantification of CFUs was carried out by recovering fungal microorganisms from skin explants and subsequent plating them following the serial dilution method to determine the number of CFUs.

Comparative Antifungal Activity

The antifungal activity was evaluated for Ketoconazole 2% (P1), the composition of example 1 (P2), and petroleum jelly (Vaseline) (P3) with respect to the inoculum concentration (C1) and control skin explants (C2).

Figure 2:
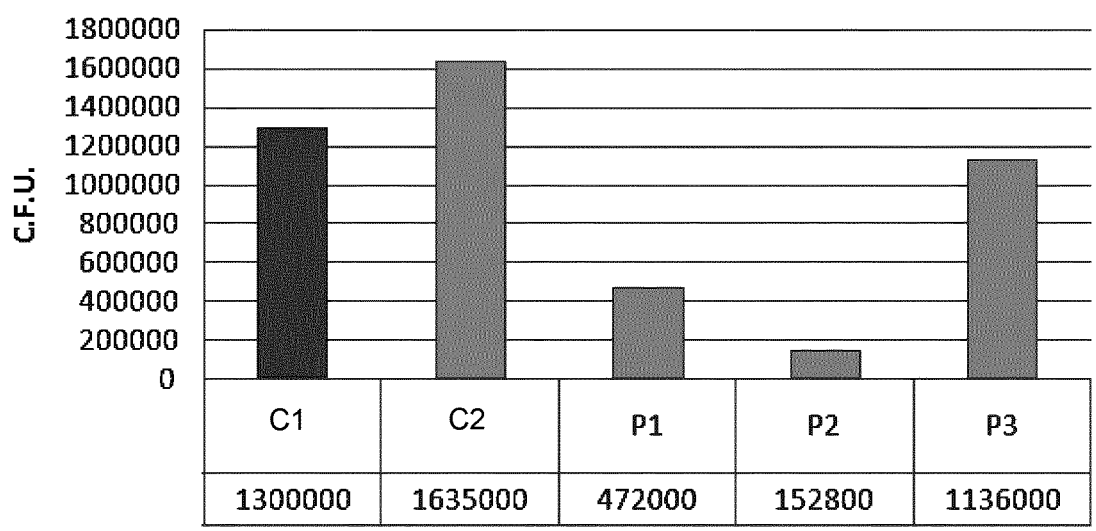
FIG. 2 shows an ex-vivo determination of the antifungal activity against *Malassezia furfur* in human skin explants of ketoconazole 2% (P1), the composition of example 1 (P2), and petroleum jelly (Vaseline) (P3).

As it can be seen in FIG. 2, the control treatment with petroleum jelly (Vaseline) (P3) did not significantly affect the growth of *M. furfur* on the skin explants. In contrast, the application of Ketoconazol 2% (P1) reduced the growth of the fungus on the explants. Most interestingly, the application of the compound of the invention (P2) elicited the biggest reduction in *M. furfur* growth, showing an efficacy that surpasses the antifungal compound ketoconazole. These results demonstrate the great potential of the compounds of the invention for treating skin fungal infections.

Antifungal activity of rhamnosoft

Human skin explants were obtained with informed consent from healthy, 40 to 55 year-old women undergoing plastic surgery (Authorisation granted by French government ethical committee according to French law L.1245 CSP). Up to 2 h from the surgery the skin was cut to a 0.8 cm2 pieces and samples were placed with dermis facing down and epidermis facing up in culture plates containing DMEM medium with antibiotics (1% pen-strep). Cultures were incubated for at least 48 hours at 37° C. under 5% CO2 for recovery prior to study initiation.

Step 1. Skin explants (Human Skin Explants) from healthy donors were altered by stripping (leading to removal of ~40% of stratum corneum thickness) to facilitate stabilization of infection by the fungus.

Step 2. The skin explants were allowed to stabilize (rested for 48 h) after stripping.

Step 3. For each treatment group test articles were applied topically at 2 mg/cm2 in a manner that was identical for all treatment groups and spread carefully using a microspatula. Skin explants in the Control group did not receive any topical treatment (control 3, C3).

Step 4. Skin explants previously coated with test articles and in Control group were inoculated by addition of a suspension of *Malassezia furfur* in the surface and incubated for 24 hours.

Step 5. After incubation period of 24 hours, the number of colony forming units (CFUs) was quantified using the direct plate method.

The antifungal activity was evaluated for piroctone olamine of comparative example 3 (P4), and the composition of example 2 (P5) with respect to control 3.

Figure 3:
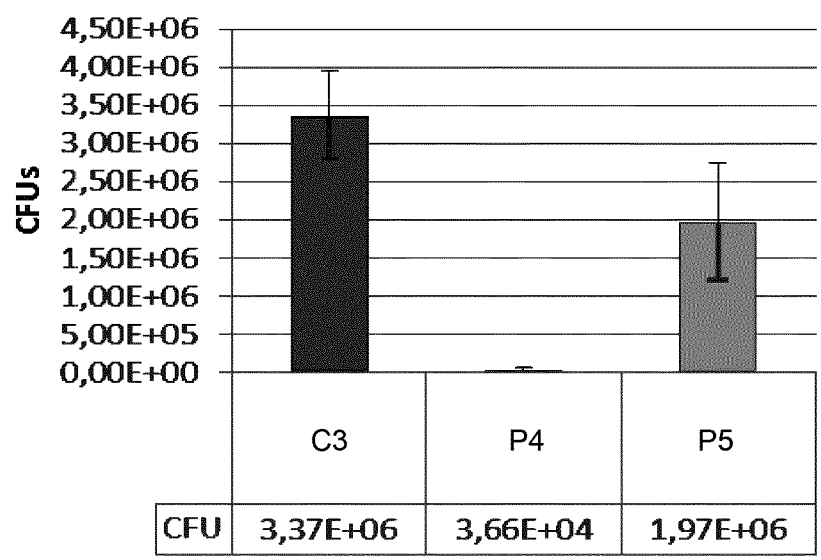
FIG. 3 shows an ex-vivo determination of the antifungal activity against *Malassezia furfur* in human skin explants of piroctone olamine (P4), and the composition of example 2 (P5).

As it can be seen in FIG. 3, the application of the compound of the invention (P5) effectively reduced the *M. furfur* growth.

The invention claimed is:

1. A method for the treatment and/or prevention of a fungal infection in a human being, comprising administering an effective amount of a rhamnose-rich polysaccharide, which comprises a repeating unit of formula (I),

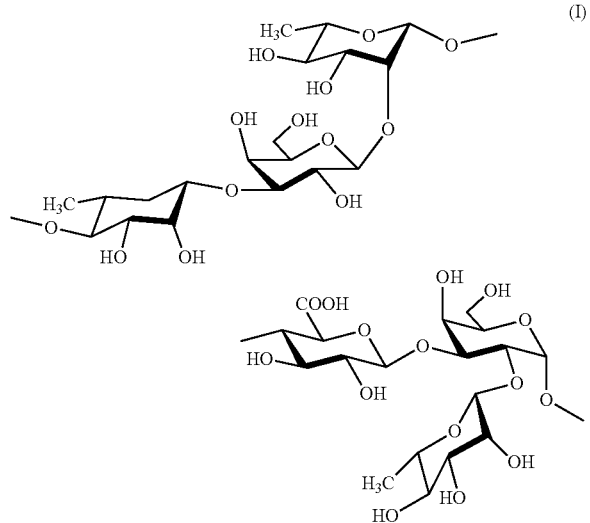

(I)

to the human being in need thereof.

2. The method according to claim 1, wherein the rhamnose-rich polysaccharide has a molecular weight from 45000 to 55000 g/mol.

3. The method according to claim 1, wherein the rhamnose-rich polysaccharide forms part of a combination comprising a further antifungal agent.

4. The method according to claim 3, wherein the further antifungal agent of the combination is piroctone olamine.

5. The method according to claim 1, wherein the rhamnose-rich polysaccharide forms part of a pharmaceutical or cosmetic composition which comprises an effective amount of the rhamnose-rich polysaccharide, together with one or more pharmaceutically or cosmetically acceptable excipients or carriers.

6. The method according to claim 5, wherein the pharmaceutical or cosmetic composition comprises a further antifungal agent.

7. The method according to claim 6, wherein the rhamnose-rich polysaccharide, and the further antifungal agent are present in amounts producing a synergistic effect.

8. The method according to claim 5, wherein the total amount of antifungal agent in the composition is equal to or lower than 0.8% w/w.

9. The method according to claim 5, wherein the total amount of antifungal agent in the composition is equal to or lower than 0.6% w/w.

10. The method according to claim 5, wherein the composition comprises Zinc pyrrolidone carboxylate (Zinc PCA), piroctone olamine, and stearyl glycyrrhetinate.

11. The method according to claim 1, wherein the fungal infection is caused by *Malassezia* species.

12. The method according to claim 1, wherein the fungal infection causes a skin disease.

13. The method according to claim 12, wherein the skin disease is seborrheic dermatitis.

* * * * *